US008603007B2

(12) United States Patent
Fu et al.

(10) Patent No.: US 8,603,007 B2
(45) Date of Patent: Dec. 10, 2013

(54) DATA BINNING METHOD AND SYSTEM FOR ESTIMATING RESPIRATORY AIRFLOW FROM BODY SOUND SIGNAL

(75) Inventors: Yongji Fu, Vancouver, WA (US); Bryan Severt Hallberg, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 789 days.

(21) Appl. No.: 12/802,334

(22) Filed: Jun. 4, 2010

(65) Prior Publication Data

US 2011/0301485 A1    Dec. 8, 2011

(51) Int. Cl.
*A61B 5/08* (2006.01)
(52) U.S. Cl.
USPC .......................................... 600/538; 600/529
(58) Field of Classification Search
USPC ................................................. 600/529–543
See application file for complete search history.

(56) References Cited

U.S. PATENT DOCUMENTS

| 5,218,969 | A | 6/1993 | Bredesen et al. | 128/710 |
|---|---|---|---|---|
| 5,853,005 | A | 12/1998 | Scanlon | 600/459 |
| 6,168,568 | B1 * | 1/2001 | Gavriely | 600/529 |
| 6,241,683 | B1 * | 6/2001 | Macklem et al. | 600/529 |
| 7,063,669 | B2 | 6/2006 | Brawner et al. | 600/532 |
| 7,477,144 | B2 | 1/2009 | Albert | 340/573.1 |
| 2003/0216659 | A1 * | 11/2003 | Brawner et al. | 600/532 |
| 2007/0032733 | A1 | 2/2007 | Burton | |
| 2008/0243017 | A1 * | 10/2008 | Moussavi et al. | 600/532 |

FOREIGN PATENT DOCUMENTS

WO    WO2006/129516    12/2006

OTHER PUBLICATIONS

"Sound." Encyclopedia Britannica. Encyclopedia Britannica Online Academic Edition. 2013. Web. Mar. 21, 2013. http://www.britannica.com/EBchecked/topic/555255/sound.*

(Continued)

*Primary Examiner* — Patricia Mallari
*Assistant Examiner* — Tiffany Weston
(74) *Attorney, Agent, or Firm* — Scot A. Reader (57) ABSTRACT

Data binning methods and systems for estimating a subject's respiratory airflow from a body sound signal detected by an acoustic sensor on the subject's body. The methods and systems operate in a configuration mode followed by a monitoring mode. In the configuration mode, a body sound signal and respiratory airflow are detected by an on-body acoustic sensor and a spirometer, respectively, over a common time period. Time-aligned body sound signal and respiratory airflow data points are then generated and assigned to bins each spanning a discrete signal range (e.g. discrete signal entropy range or signal amplitude range). Respiratory airflow estimation data (e.g. mean airflow and standard deviation) are then calculated for each bin and an entry for each bin associating the discrete range and the estimation data is stored in a lookup table. Then, in the monitoring mode, the lookup table is accessed using subsequent body sound signal readings (e.g. taken in the field or at home) to provide respiratory airflow estimates without further need for a spirometer.

20 Claims, 6 Drawing Sheets

(56) References Cited

OTHER PUBLICATIONS

Yadollahi, et al. "A Robust Method for Estimating Respiratory Flow Using Tracheal Sounds Entropy." IEEE Transactions on Biomedical Engineering. Apr. 2006. vol. 53, No. 4. pp. 662-668.*

G. Wodicka et al., "A Model of Acoustic Transmission in the Respiratory System," IEEE Trans. Biomed. Eng. Sep. 1989 36(9): 925-34.

A. Yadollahi et al., A Robust Method for Estimating Respiratory Flow Using Tracheal Sound Entropy, IEEE Trans. Biomed. Eng. Apr. 2006 53(4): 662-68.

R. Beck et al., "Measurements and Theory of Normal Tracheal Breath Sounds," Annals of Biomed. Eng. Oct. 2005 33(10): 1344-51.

* cited by examiner

DATA BINNING METHOD AND SYSTEM FOR ESTIMATING RESPIRATORY AIRFLOW FROM BODY SOUND SIGNAL

BACKGROUND OF THE INVENTION

The present invention relates to respiratory monitoring and, more particularly, to methods and systems for estimating a subject's respiratory airflow from a body sound signal detected by an acoustic sensor on the subject's body.

Respiratory airflow data, such as current respiratory airflow rate data, peak expiratory flow rate (PEFR) data and forced expiratory volume in the first second (FEV1) data, can be used to diagnose and treat respiratory ailments, such as asthma and chronic obstructive pulmonary disease (COPD), and to monitor the respiratory health of people who suffer from respiratory ailments. Such data can also be useful in other contexts, such as in detecting airborne hazards in occupational settings.

Spirometry is considered the gold standard for accurate and repeatable measurement of respiratory airflow. However, spirometry is not well-adapted for monitoring of a human subject in the field as he or she goes about his or her daily activities, or even for at-home monitoring. Spirometry requires access to a spirometer having a mouthpiece attached to a tube, which is in turn attached to electronic sensors, which are in turn attached to a computer that measures respiratory airflow parameters. Moreover, to get an accurate reading from a spirometer, a subject must often wear nose clips to ensure that breathing is done through the mouth, and must sit up straight, with feet against the floor, and with head facing forward.

Recent attempts have been made to estimate respiratory airflow from a body sound signal detected by an on-body acoustic sensor, which can be worn by a subject as he or she performs a daily routine, and also at home. Some of these attempts have taken advantage of a general correlation between body sound signal amplitude or entropy and respiratory airflow. In one approach, a body sound signal and respiratory airflow are detected by an acoustic sensor mounted at a subject's trachea and a spirometer, respectively, over a common time frame. Time-aligned signal entropy and respiratory airflow data points are fed into an analytical model that produces a best fit equation describing the relationship between signal entropy and respiratory airflow across the entire spectrum of measured entropies and airflows. Subsequent body sound signal readings (e.g. taken in the field or at home) are thereafter plugged-in to the best fit equation to yield estimates of respiratory airflow, without any further need for a spirometer.

Unfortunately, known approaches to estimating respiratory airflow from a body sound signal detected by an on-body acoustic sensor have so far met with only limited success. No best fit equation describing the relationship between a characteristic of a body sound signal and respiratory airflow has proven accurate for the general population, or across an entire spectrum of body sound signals and respiratory airflows experienced by a given subject. For example, a best fit equation that is accurate for a given subject at low airflows will be inaccurate for the subject at high airflows, or vice versa.

SUMMARY OF THE INVENTION

The present invention provides data binning methods and systems for estimating a human subject's respiratory airflow from a body sound signal detected by an acoustic sensor on the subject's body. The methods and systems operate in a configuration mode followed by a monitoring mode. In the configuration mode, a body sound signal and respiratory airflow are detected by an on-body acoustic sensor and a spirometer, respectively, over a common time period. Time-aligned body sound signal and respiratory airflow data points are then generated and assigned to bins each spanning a discrete signal range (e.g. discrete signal entropy range or signal amplitude range). Respiratory airflow estimation data (e.g. mean airflow and standard deviation) are then calculated for each bin and an entry for each bin associating the discrete signal range and the estimation data is stored in a lookup table. Then, in the monitoring mode, the lookup table is accessed using subsequent body sound signal readings (e.g. taken in the field or at home) to provide respiratory airflow estimates without further need for a spirometer. By segmenting the spectrum of body sound signals and respiratory airflows experienced by the subject into small bins for purposes of respiratory airflow estimation, the methods and systems of the present invention provide respiratory airflow estimates that exhibit reduced error as compared to estimates provided by prior approaches that rely on best fit equations. Moreover, the methods and systems of the present invention enable provision of confidence data for each estimate.

In one aspect of the invention, a method for estimating respiratory airflow on a respiratory monitoring device comprises the steps of receiving on the respiratory monitoring device body sound signal data from a first source and respiratory airflow data from a second source, generating on the respiratory monitoring device time-aligned data points from the body sound signal data and the respiratory airflow data, assigning on the respiratory monitoring device each data point to one of a plurality of bins each spanning a discrete body sound signal range, calculating on the respiratory monitoring device respiratory airflow estimation data for each bin using the data points assigned to that bin, populating on the respiratory monitoring device a lookup table with an entry for each bin associating the discrete body sound signal range for that bin and the estimation data for that bin, acquiring on the respiratory monitoring device additional body sound signal data, retrieving on the respiratory monitoring device from the lookup table estimation data corresponding to the additional body sound signal data, and outputting on the respiratory monitoring device respiratory airflow output data based on the estimation data.

In some embodiments, the discrete body sound signal range for each bin is a signal entropy range.

In some embodiments, the discrete body sound signal range for each bin is a signal amplitude range.

In some embodiments, the estimation data comprise a mean respiratory airflow.

In some embodiments, the estimation data comprise a standard deviation about a mean respiratory airflow.

In some embodiments, the output data comprise a current respiratory airflow rate estimate.

In some embodiments, the output data comprise a PEFR estimate.

In some embodiments, the output data comprise a FEV1 estimate.

In some embodiments, the output data comprise confidence data for a respiratory airflow estimate.

In some embodiments, the respiratory monitoring device is portable.

In some embodiments, the first source is an acoustic sensor.

In some embodiments, the second source is a spirometer.

In some embodiments, the steps of acquiring additional body sound signal data, retrieving from the lookup table estimation data corresponding to the additional body sound signal data, and outputting output data based on the estimation data are performed continually.

In another aspect of the invention, a respiratory monitoring device comprises a first input interface, a second input interface, a database, an output interface and a processor communicatively coupled with the first and second input interfaces, the output interface and the database, wherein the device receives body sound signal data on the first input interface and respiratory airflow data on the second input interface, and under control of the processor generates time-aligned data points from the body sound signal data and the respiratory airflow data, assigns each data point to one of a plurality of bins each spanning a discrete body sound signal range, calculates respiratory airflow estimation data for each bin using the data points assigned to that bin, populates a lookup table in the database with an entry for each bin associating the discrete body sound signal range for that bin and the estimation data for that bin, receives additional body sound signal data via the first input interface, retrieves from the lookup table estimation data corresponding to the additional body sound signal data, and outputs on the output interface output data based on the estimation data.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
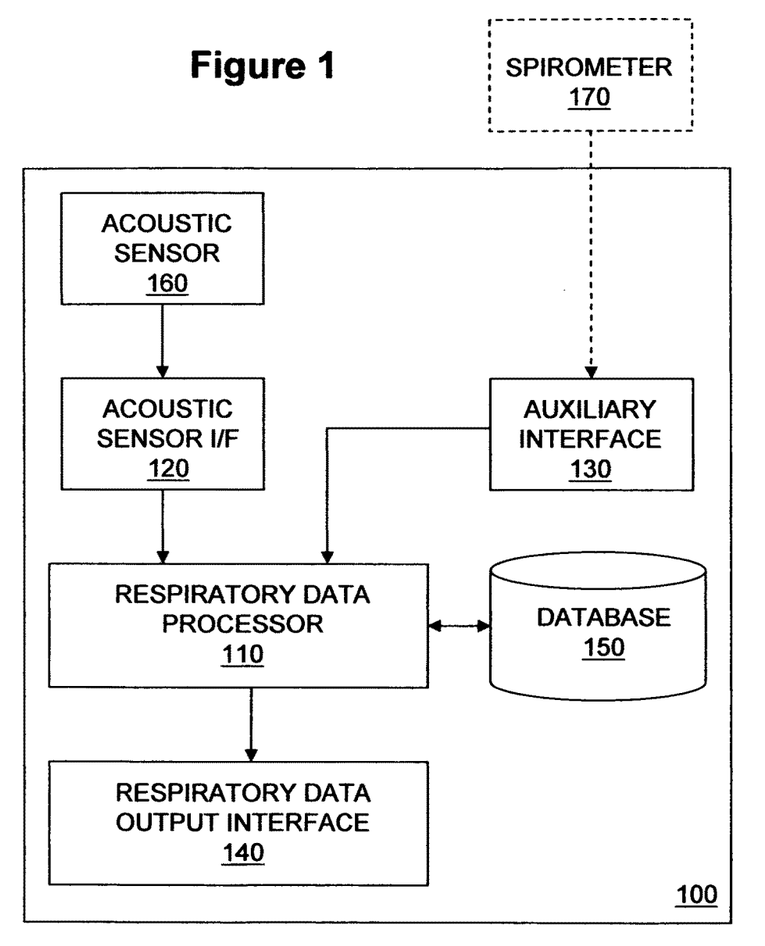
FIG. 1 shows a respiratory monitoring device in some embodiments of the invention.

FIG. 1 shows a respiratory monitoring device 100 in some embodiments of the invention. Monitoring device 100 is a portable ambulatory health monitoring device that can either monitor a human subject's physiological well-being in real-time as he or she performs daily activities, or monitor the subject's physiological well-being at home by occasionally testing respiratory airflow parameters, or both. In other embodiments, a fixed position monitoring device may be used.

Monitoring device 100 includes a respiratory data processor 130 communicatively coupled with an acoustic sensor interface 120, an auxiliary interface 130, a respiratory data output interface 140 and a database 150. Processor 110 is a microprocessor that executes under software control, although in other embodiments an application specific integrated circuit (ASIC) based processor may be used. Monitoring device 110 also has an acoustic sensor 160 communicatively coupled with acoustic sensor interface 120.

Monitoring device 100 operates in a configuration mode and a monitoring mode. While in the configuration mode, a lookup table on database 150 having entries mapping body sound signal data to respiratory airflow estimation data is populated. While in the monitoring mode, entries in the lookup table are accessed using body sound signal data to retrieve respiratory airflow estimation data that is used, in turn, to generate respiratory airflow output data outputted on output interface 140.

Acoustic sensor 160 is operative in both the configuration mode and monitoring mode. Acoustic sensor 160 detects body sounds at a detection point, such as a trachea, chest or back of the subject and transmits a body sound signal to acoustic sensor interface 120 in the form of an electrical signal generated from detected lung sounds. Acoustic sensor 160 may include, for example, a sound transducer positioned on the body of the subject.

Acoustic sensor interface 120 receives the body sound signal from acoustic sensor 160, amplifies and performs analog/digital (A/D) conversion on the body sound signal, and transmits the body sound signal to processor 110. Amplification and A/D conversion may be performed, by way of example, by serially arranged amplifier and A/D conversion stages. In some embodiments, the body sound signal is also subjected at acoustic sensor interface 120 to automatic gain control. In any event, the body sound signal transmitted by acoustic sensor interface 120 to processor 110 remains unfiltered.

A spirometer 170 is also operative in the configuration mode. Spirometer 170 is connected to auxiliary interface 130 while monitoring device 100 is in the configuration mode and is generally disconnected from auxiliary interface 130 while monitoring device is in the monitoring mode. Spirometer 170 includes a mouthpiece attached to a tube, which is in turn attached to electronic sensors, which are in turn attached to a computer, which is in turn connected to auxiliary interface 130. The computer generates respiratory airflow data from an electrical signal generated by the electronic sensors in response to breathing into the tube by the subject, and transmits the respiratory airflow data to auxiliary interface 130.

Auxiliary interface 130 receives the respiratory airflow data from spirometer 170 and transmits the respiratory airflow data to processor 110. Auxiliary interface 130 may be, for example, a universal serial bus (USB) interface.

Processor 110 is operative in both the configuration mode and the monitoring mode. While monitoring device 100 is in the configuration mode, processor 110 populates a lookup table on database 150 with entries mapping body sound signal data to respiratory airflow estimation data. While in the monitoring mode, processor 110 accesses entries in the lookup table on database 150 to retrieve respiratory airflow estimation data, and uses the respiratory airflow estimation data to generate respiratory airflow output data, such as estimates of current respiratory airflow rate, PEFR and/or FEV1. Processor 110 transmits respiratory airflow output data to output interface 140.

Output interface 140 is operative in the monitoring mode. Output interface 140 includes a display screen for displaying to the subject respiratory airflow output data received from processor 110.

While in the monitoring mode, processor 110 may also transmit respiratory airflow output data via auxiliary interface 130 to an external data management system connected to monitoring device 110 that stores the data and/or a remote monitoring device, such as a monitoring device at a clinician facility. In such embodiments, auxiliary interface 130 provides a second output interface.

Figure 5:
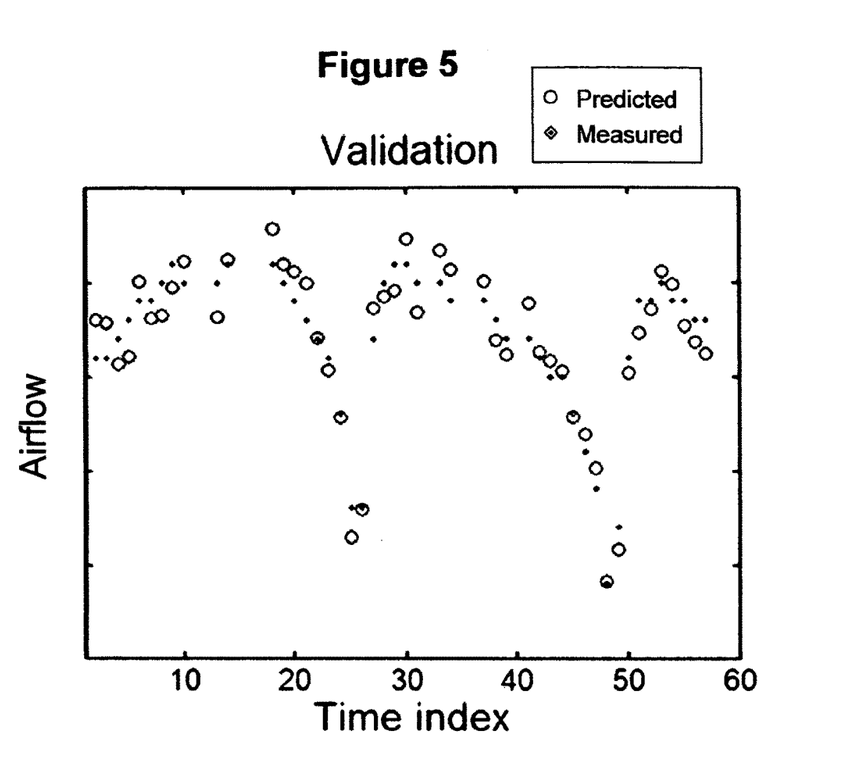
FIG. 5 is a scatter plot showing predicted and measured respiratory airflow data points in some embodiments of the invention.
Figure 6:
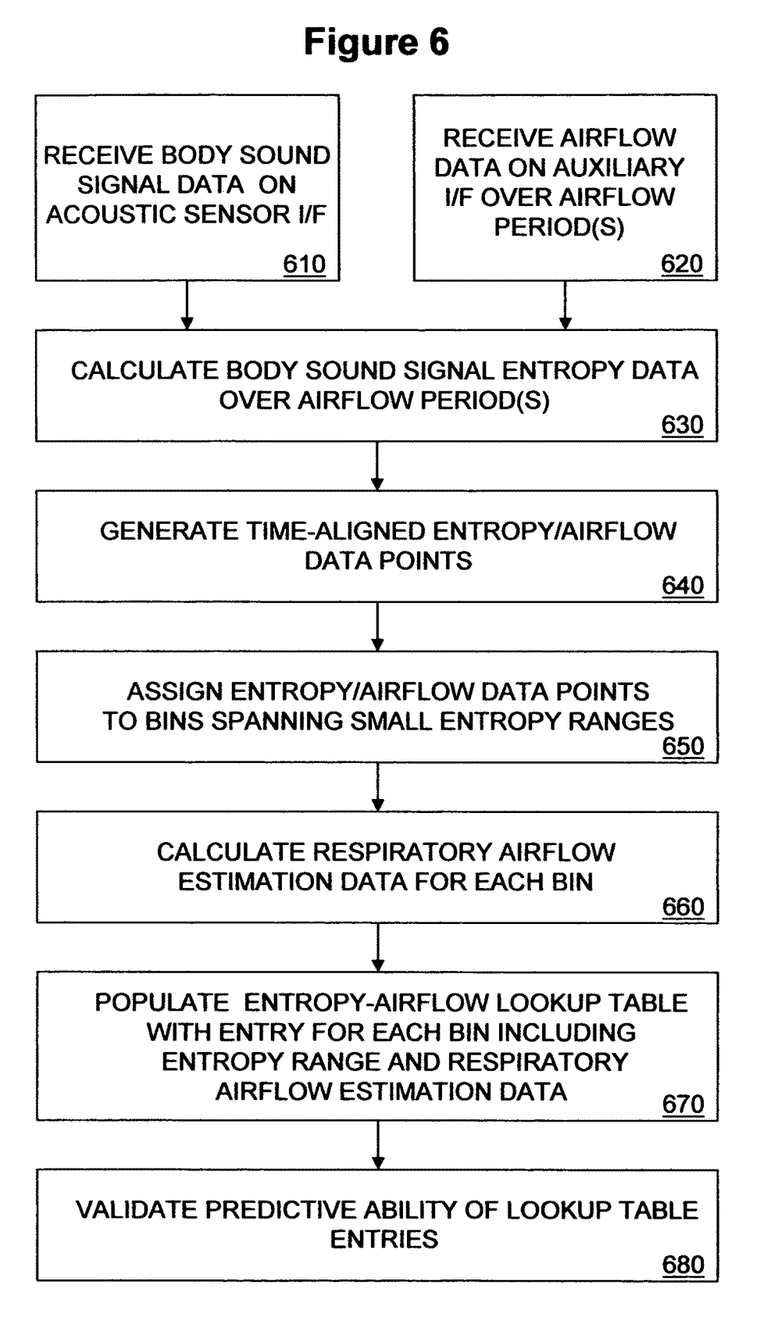
FIG. 6 shows configuration steps of a method for estimating respiratory airflow on a respiratory monitoring device in some embodiments of the invention.

FIG. 6 shows configuration steps of a method for estimating respiratory airflow on monitoring device 100 in some embodiments of the invention. These steps are performed under control of processor 110 and will be described in conjunction with FIGS. 2-5.

Figure 2:
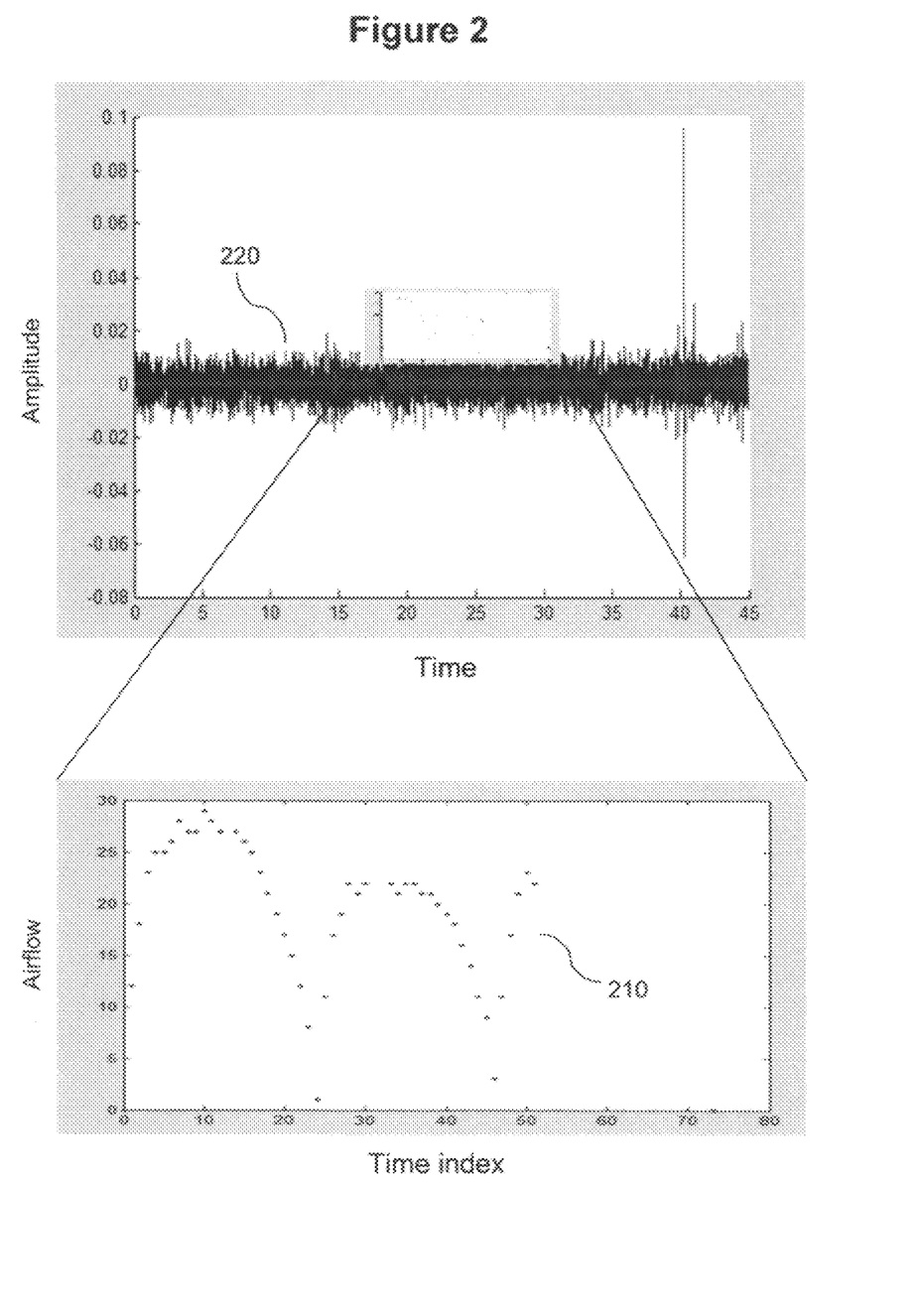
FIG. 2 shows respiratory airflow data overlaid on body sound signal data in some embodiments of the invention.

Initially, body sound signal data are received via acoustic sensor interface 120 (610) The body sound signal data are an amplified and digitized version of a body sound signal sourced by acoustic sensor 160 positioned on the body of the subject. Respiratory airflow data are separately received from spirometer 170 via auxiliary interface 130 (620). In some embodiments, the body sound signal data and the respiratory airflow data are time-stamped either before or after arrival at monitoring device 100. FIG. 2 shows respiratory airflow data 210 overlaid on acoustic signal data 220 in some embodiments of the invention. As shown in the figure, body sound signal data 220 are supplied on a near-continuous basis, whereas respiratory airflow data 210 are generated by over one or more discrete airflow periods in which the subject undergoes normal and/or forced breathing through a tube and are supplied intermittently.

The decision to use normal or forced breathing in the configuration mode depends on the respiratory airflow parameter that will be monitored in the monitoring mode. For example, forced breathing may be used if the parameter to be monitored is PEFR or FEV1, whereas normal breathing may be used if the parameter to be monitored is current respiratory airflow. In some embodiments, both normal and forced breathing are used in the configuration mode to produce a complete spectrum that enables various types of respiratory airflow parameters to be monitored in the monitoring mode.

Next, body sound signal entropy data for the airflow periods are calculated using the body sound signal data (630). Entropy of the body sound signal at detected points may be calculated using the Shannon or Renyi method, and provides a measure of the variation of the probability density function of lung sound in the presence of heart sound. Time stamps from the detected points in the body sound signal data are transferred to the body sound signal entropy data to add a time reference.

Figure 3:
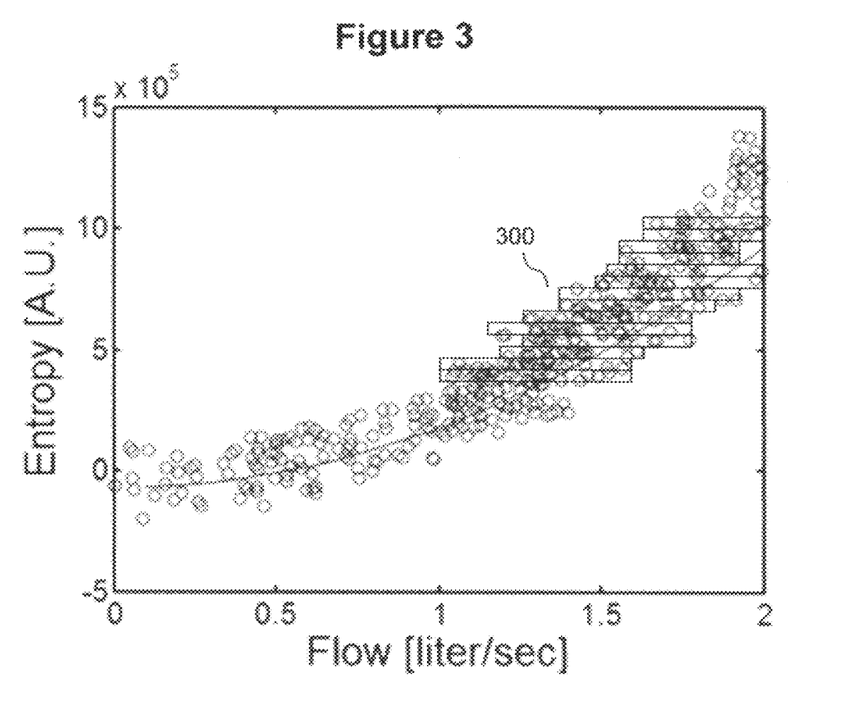
FIG. 3 is a scatter plot showing data bins spanning discrete body sound signal entropy ranges overlaid on time-aligned body sound signal entropy and respiratory airflow data points in some embodiments of the invention.

Next, time-aligned signal entropy-airflow data points are generated from the body sound signal entropy data and the respiratory airflow data (640). FIG. 3 shows a scatter plot of time-aligned signal entropy and airflow data points generated in some embodiments of the invention. The x-axis is respiratory airflow rate in liters per second and the y-axis is signal entropy in aptitude units (an arbitrary unit of measure).

A line corresponding to a best fit equation for the plotted data is also shown in FIG. 3 for illustrative purposes. As is readily apparent, the estimation error of the best fit equation increases considerably at signal entropies above two aptitude units, which corresponds to respiratory airflow rates in excess of one liter per second. Data bins 300 are introduced to facilitate creation of an alternative description of the relationship between signal entropy and respiratory airflow rate.

Accordingly, next, each time-aligned entropy-airflow data point is assigned to one of a plurality of data bins 300, each of which spans a discrete signal entropy range (650). Each bin covers a discrete, fixed signal entropy range and a variable respiratory airflow range that depends on the distribution of the data points within the range. In the figure, fourteen bins 300 are shown covering, in the aggregate, the range from about 3.5 to 10.5 aptitude units; however, in practice a number of bins will be used that is sufficiently large that every data point fits within a bin.

Next, respiratory airflow estimation data, including a mean airflow and standard deviation about the mean airflow assuming a normal distribution, are calculated for each bin (660).

Figure 4:
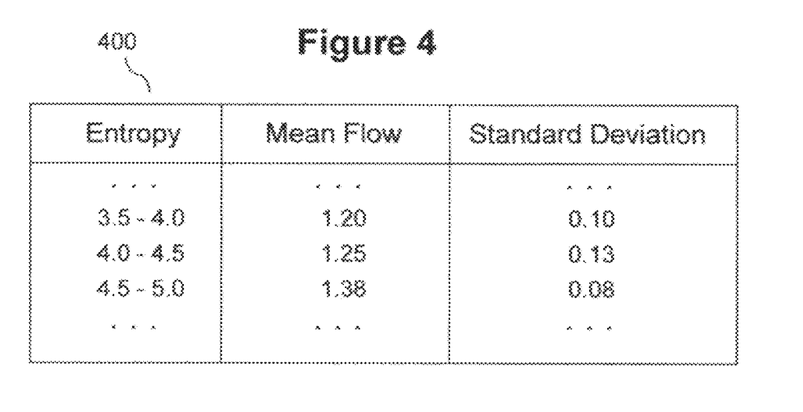
FIG. 4 shows an entropy-airflow lookup table in some embodiments of the invention.

Next, an entropy-airflow lookup table in database 150 is populated with an entry for each bin that includes the discrete signal entropy range covered by the bin and corresponding respiratory airflow estimation data, namely, a mean airflow and a standard deviation about the mean airflow calculated from data points that fit within the bin (670). FIG. 4 shows an entropy-airflow lookup table 400 in some embodiments of the invention. Lookup table 400 has an entry for each bin that specifies a signal entropy range, a mean airflow and a standard deviation. By way of example, data points in the bin covering the signal entropy range between 3.5 and 4.0 aptitude units have a mean airflow of 1.20 liters per second with a standard deviation from the mean of 0.10.

Next, the predictive ability of the lookup table entries may be validated (680). In an exemplary validation, additional time-aligned body sound signal data and respiratory airflow data are detected using acoustic sensor 160 and spirometer 170, respectively. Signal entropy data are calculated from the body sound signal data and used as an index into lookup table 400 to retrieve mean airflow data. The mean airflow data, which is the predicted result, is compared with the airflow data detected by spirometer 170, which is the measured result, to validate the lookup table entries. FIG. 5 is a scatter plot generated in a validation study comparing the predicted and measured respiratory airflow data points. Successful validation marks the end of the configuration mode.

Figure 7:
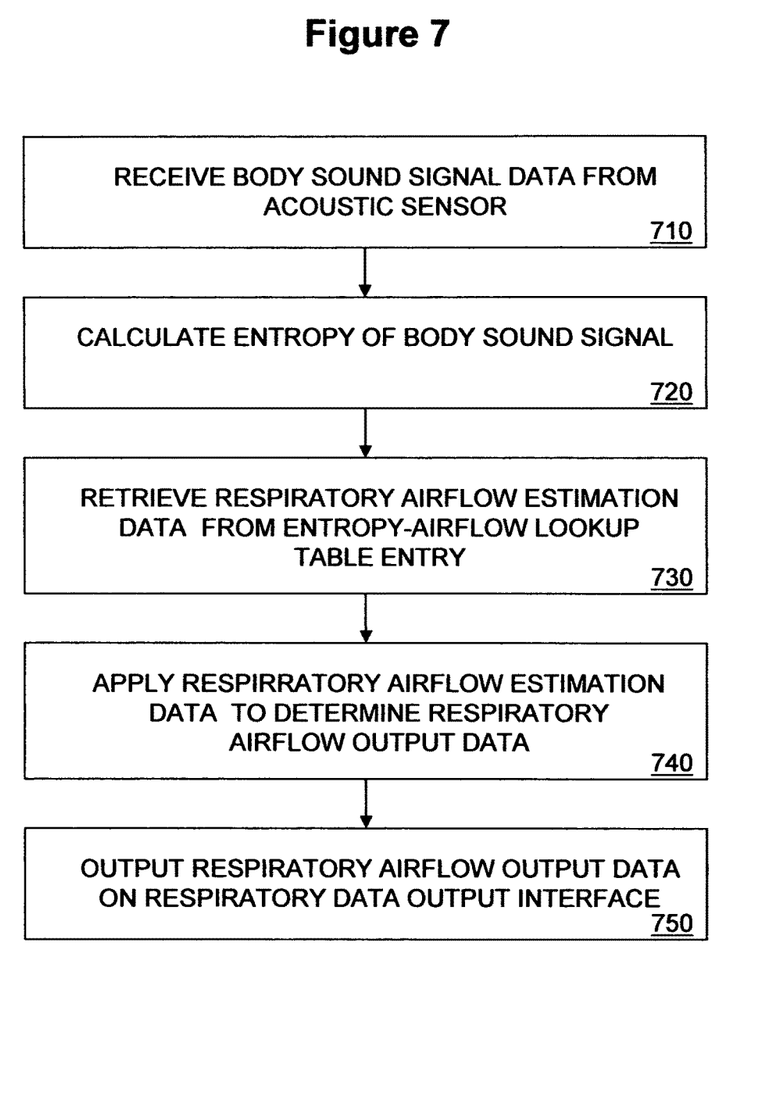
FIG. 7 shows monitoring steps of a method for estimating respiratory airflow on a respiratory monitoring device in some embodiments of the invention.

FIG. 7 shows monitoring steps of a method for estimating respiratory airflow on monitoring device 100 in some embodiments of the invention. These steps follow the configuration steps and are performed under control of processor 110 in conjunction with output interface 140. These steps are typically performed in the field while monitoring the human subject's physiological well-being in real-time as he or she performs daily activities, or at home during occasional testing of respiratory airflow parameters (e.g. PEFR, FEV1). Spirometer 170 is not required to perform these steps, and is typically not connected to monitoring device 100 while these steps are performed.

Initially, body sound signal data are received via acoustic sensor interface 120 over a detection period (710). The body sound signal data are an amplified and digitized version of a body sound signal sourced by acoustic sensor 160 positioned on the body of the subject. The body sound signal may be detected during normal or forced breathing, depending on the respiratory airflow parameter presently sought to be monitored. For example, forced breathing may be used if the parameter presently sought to be monitored is PEFR or FEV1, whereas normal breathing may be used if the parameter presently sought to be monitored is current respiratory airflow rate.

Next, body sound signal entropy data are calculated from the body sound signal data over the detection period (720), using the Shannon or Renyi method by way of example. The signal entropy data may have one or more data points.

Next, respiratory airflow estimation data, including mean airflow and optionally standard deviation, are retrieved from lookup table 400 using the entropy data as an index (730). For example, if the body sound signal entropy over the detection period includes data points at 3.7, 4.4 and 4.8 aptitude units, lookup table 400 would return mean flow values of 1.20, 1.25 and 1.38 liters per second and standard deviation values of 0.10, 0.13 and 0.08, respectively.

Next, the respiratory airflow estimation data are used to determine respiratory airflow output data (740). Respiratory airflow output data may include, by way of example, a current respiratory airflow rate estimate, a PEFR estimate or an FEV1 estimate determined based at least in part on one or more mean airflow values in the respiratory airflow estimation data. Respiratory airflow output data may further include, for example, confidence data for the respiratory airflow estimate determined based at least in part on one or more standard deviation values in the respiratory airflow estimation data. Confidence data may take the form of a confidence score that is inversely related to standard deviation. In some embodiments, where confidence in a respiratory airflow estimate is sufficiently low, output data may include an indication to that effect in lieu of the estimate.

Figure 8:
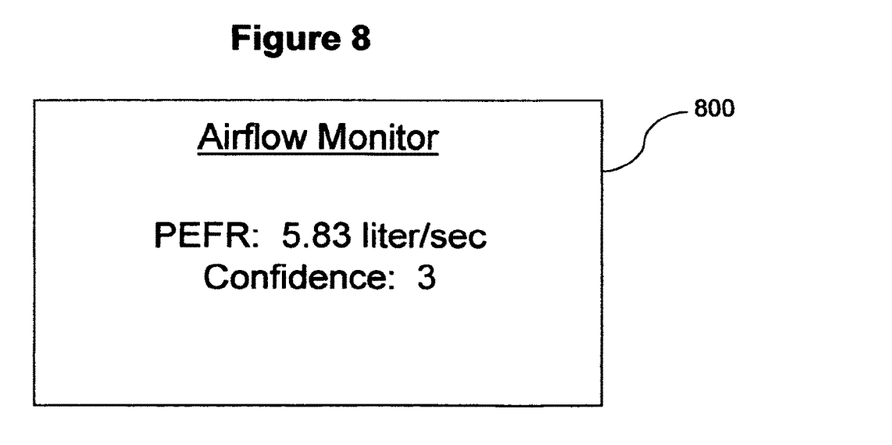
FIG. 8 shows a display screen with respiratory airflow output data in some embodiments of the invention.

Finally, the respiratory airflow output data are outputted on output interface 140 (750). For example, the respiratory airflow output data may be displayed to the subject on a display screen of output interface 140, transmitted via auxiliary interface 130 to an external data management system connected to monitoring device 110 that stores the data and/or transmitted to a remote monitoring device, such as a monitoring device at a clinician facility. FIG. 8 shows an exemplary display screen 800 displaying respiratory airflow output data. Screen 800 presents a PEFR determined from a plurality of mean airflow values and a confidence score determined from one or more standard deviation values.

It will be appreciated by those of ordinary skill in the art that the invention can be embodied in other specific forms without departing from the spirit or essential character hereof. For example, in some embodiments, the amplitude of the body sound signal is used instead of the entropy of the body sound signal. More particularly, while in the configuration mode, the lookup table is populated with entries associating discrete signal amplitude ranges of the body sound signal and respiratory airflow estimation data, and while in the monitoring mode, the lookup table is accessed using additional body sound signal amplitude data to retrieve respiratory airflow estimation data, which is thereafter applied to determine respiratory airflow output data. The present description is therefore considered in all respects to be illustrative and not restrictive. The scope of the invention is indicated by the appended claims, and all changes that come with in the meaning and range of equivalents thereof are intended to be embraced therein.

What is claimed is:

1. A method for estimating respiratory airflow on a respiratory monitoring device, comprising the steps of:
    receiving on the respiratory monitoring device body sound signal data from a first source and respiratory airflow data from a second source;
    generating on the respiratory monitoring device time-aligned data points from the body sound signal data and the respiratory airflow data;
    assigning on the respiratory monitoring device each of the time-aligned data points to one of a plurality of bins each spanning a discrete body sound signal range;
    calculating on the respiratory monitoring device without invoking best fit analysis respiratory airflow estimation data for each bin using the time-aligned data points assigned to that bin;
    populating on the respiratory monitoring device a lookup table with an entry for each bin associating the discrete body sound signal range for that bin and the estimation data for that bin;
    acquiring on the respiratory monitoring device additional body sound signal data;
    retrieving on the respiratory monitoring device from the lookup table estimation data corresponding to the additional body sound signal data; and
    outputting on the respiratory monitoring device respiratory airflow output data based on the estimation data.

2. The method of claim 1, wherein the discrete body sound signal range for each bin is a signal entropy range.

3. The method of claim 1, wherein the discrete body sound signal range for each bin is a signal amplitude range.

4. The method of claim 1, wherein the estimation data comprise a mean respiratory airflow.

5. The method of claim 1, wherein the estimation data comprise a standard deviation about a mean respiratory airflow.

6. The method of claim 1, wherein the output data comprise a current respiratory airflow rate estimate.

7. The method of claim 1, wherein the output data comprise a peak expiratory flow rate (PEFR) estimate.

8. The method of claim 1, wherein the output data comprise a forced expiratory volume in the first second (FEV1) estimate.

9. The method of claim 1, wherein the output data comprise confidence data for a respiratory airflow estimate.

10. The method of claim 1, wherein the respiratory monitoring device is portable.

11. The method of claim 1, wherein the first source is an acoustic sensor.

12. The method of claim 1, wherein the second source is a spirometer.

13. The method of claim 1, wherein the steps of acquiring additional body sound signal data, retrieving from the lookup table estimation data corresponding to the additional body sound signal data, and outputting output data based on the estimation data are performed continually.

14. A respiratory monitoring device, comprising:
    a first input interface;
    a second input interface;
    a database;
    an output interface; and
    a processor communicatively coupled with the first and second input interfaces, the output interface and the database, wherein the device receives body sound signal data on the first input interface and respiratory airflow data on the second input interface, and under control of the processor generates time-aligned data points from the body sound signal data and the respiratory airflow data, assigns each of the time-aligned data points to one of a plurality of bins each spanning a discrete body sound signal range, calculates without invoking best fit analysis respiratory airflow estimation data for each bin using the time-aligned data points assigned to that bin, populates a lookup table in the database with an entry for each bin associating the discrete body sound signal range for that bin and the estimation data for that bin, receives additional body sound signal data via the first input interface, retrieves from the lookup table estimation data corresponding to the additional body sound signal data, and outputs on the output interface output data based on the estimation data.

15. The device of claim 14, wherein the discrete body sound signal range for each bin is a signal entropy range.

16. The device of claim 14, wherein the discrete body sound signal range for each bin is a signal amplitude range.

17. The device of claim 14, wherein the estimation data comprise a mean respiratory airflow.

18. The device of claim 14, wherein the estimation data comprise a standard deviation about a mean respiratory airflow.

19. The device of claim 14, wherein the output data comprise one of a current respiratory airflow rate estimate, a PEFR estimate or a FEV1 estimate.

20. The device of claim 14, wherein the body sound signal data and the additional body sound signal data are sourced by an acoustic sensor and the respiratory airflow data are sourced by a spirometer.

* * * * *